(12) United States Patent
Doshi et al.

(10) Patent No.: US 8,778,013 B2
(45) Date of Patent: Jul. 15, 2014

(54) RE-ESTABLISHMENT OF BLOOD FLOW IN BLOCKED HUMAN ARTERIES BY TRANSFERRING NANO-ENCAPSULATED DRUG THROUGH MEDICAL DEVICES, DESIGNED FOR THE SAME AND RELEASING THE NANO-ENCAPSULATED DRUG IN HUMAN ARTERY WITH BODY PH

(75) Inventors: Manish Doshi, Surat (IN); Divyesh Sherdiwala, Surat (IN); Prakash Sojitra, Surat (IN); Ashwin Vyas, Amreli (IN); Pankaj Gandhi, Surat (IN); Zagabathuni Venkata Panchakshari Murthy, Surat (IN)

(73) Assignee: Envision Scientific Private Ltd, Surat (IN)

( * ) Notice: Subject to any disclaimer, the term of this patent is extended or adjusted under 35 U.S.C. 154(b) by 534 days.

(21) Appl. No.: 12/920,818

(22) PCT Filed: May 21, 2010

(86) PCT No.: PCT/IN2010/000347
§ 371 (c)(1),
(2), (4) Date: Sep. 2, 2010

(87) PCT Pub. No.: WO2010/137037
PCT Pub. Date: Dec. 2, 2010

(65) Prior Publication Data
US 2011/0264188 A1    Oct. 27, 2011

(30) Foreign Application Priority Data
May 29, 2009    (IN) .......................... 1324/MUM/2009

(51) Int. Cl.
*A61F 2/06*    (2013.01)

(52) U.S. Cl.
USPC .................... 623/1.42; 623/1.43; 623/1.44

(58) Field of Classification Search
None
See application file for complete search history.

(56) References Cited

U.S. PATENT DOCUMENTS

| 5,102,402 A | 4/1992 | Dror et al. |
| 2005/0095267 A1* | 5/2005 | Campbell et al. ............. 424/425 |
| 2005/0129727 A1* | 6/2005 | Weber et al. .................. 424/423 |

FOREIGN PATENT DOCUMENTS

CN        101209348        7/2008

OTHER PUBLICATIONS

"PCT International Search Report", Application No. PCT/IN2010/000347 Dec. 2, 2010, 5 pages.

* cited by examiner

*Primary Examiner* — David H Willse
*Assistant Examiner* — Tiffany Shipmon
(74) *Attorney, Agent, or Firm* — Timberline Patent Law Group PLLC (57) ABSTRACT

A drug-delivering insertable medical device for treating a medical condition associated with a body lumen is disclosed. The drug-delivering insertable medical device includes an outer surface coated with two or more nano-carriers having two or more average diameters. A nano-carrier of the two or more nano-carriers has an average diameter suitable for penetrating one or more layers of two or more layers of the body lumen. The nano-carrier includes a drug surrounded by an encapsulating medium. The encapsulating medium includes one or more of a biological agent, a blood excipient, and a phospholipid.

17 Claims, 6 Drawing Sheets

RE-ESTABLISHMENT OF BLOOD FLOW IN BLOCKED HUMAN ARTERIES BY TRANSFERRING NANO-ENCAPSULATED DRUG THROUGH MEDICAL DEVICES, DESIGNED FOR THE SAME AND RELEASING THE NANO-ENCAPSULATED DRUG IN HUMAN ARTERY WITH BODY PH

FIELD OF THE INVENTION

The invention generally relates to a medical device for administrating a drug to a target site in a body lumen. More specifically, the invention relates to a drug-delivering insertable medical device coated with nano-carriers of one or more drugs for efficient delivery of the one or more drugs across various layers of a blood vessel.

BACKGROUND OF THE INVENTION

Stents and other medical devices are used for re-establishment of a proper blood flow in a blocked artery in interventional cardiological procedures, such as, percutaneous transluminal coronary angioplasty. However, the existing interventional cardiological procedures and cardiological medical devices used in these procedures are associated with phenomenon like restenosis. In order to reduce the instances of restenosis that occur following angioplasty procedures or stent deployment Drug Eluting Stents (DESs) are often used. The current DESs are loaded with drugs with the help of polymers. The polymers may trigger inflammation at a site where the DESs are implanted. In certain instances, the inflammation triggered by the DESs may be more severe than the inflammation that is caused by bare metal stents owing to the presence of polymers in the DESs. The inflammation triggered by the polymers may in turn lead to thrombus formation because of body's physiological immune response. The thrombus thus formed may be an acute thrombus or a sub-acute thrombus. The thrombus may further aggravate resulting into blockage of the artery. In addition, the DESs with non-degradable polymers are associated with late inflammation reactions, thereby resulting in late thrombus formation. Thus, the polymers used for loading the drugs on the DESs may lead to restenosis.

In order to avoid the inflammation that is associated with the use of the polymers for loading the drug on the stent, the drug may be loaded, on surface of the stent without using polymers. However, the methods for loading the drug on the surface of the stent without using the polymers that are known in the art are based on modifying the surface of the stent.

In addition, the presence of one or more drugs and the polymers on an inner surface of the stent results in a delayed healing or an improper healing of the lesions as compared to the bare metal stents. A long-term anti-platelet (e.g. Clopidrogel) therapy is generally advised in patients with the delayed healing or the improper healing. The anti-platelet therapy is also associated with side effects and thus is not advisable for long-term.

Further, the particle sizes of the drugs as well as the polymers that are coated on the DESs are larger than the sizes of the tissue pores at a target site. Therefore, a substantial amount of the drugs remain unabsorbed. The unabsorbed drugs may get washed away in blood stream and may produce side effects. For example, currently used DESs are loaded with more than 100 micro-grams of a drug out of which, only 12 nanogram to 25 nanogram of the drug penetrates the tissues of the artery. Rest of the drug is either washed away in the blood stream from the inner surface of DESs or is released over time.

Further, the currently used DESs are associated with phenomenon like focal restenosis and edge restenosis. One of the major reasons for focal restenosis is that some portions of the lesion are adequately supplied with the drug by the DESs while some portions of the lesion (region not covered by the DES) are very poorly or not at all supplied with the drug by the DESs. The portions of the lesion that are adequately supplied with the drug may possibly remain less prone to restenosis as compared with the portions of the lesion that are poorly supplied or not at all supplied with the drug.

In the current DESs, the drug is coated on the metal surface. The amount of the drug that reaches the lesion is generally equal to a metal to artery ratio. The metal to artery ratio for the current DESs generally ranges from 10% to 20%. Thus, only 10% to 20% of the lesion is supplied with the drug. Whereas, the remaining 80% to 90% of the lesion is either very poorly supplied with the drug or not at all supplied with the drug. Further, owing to a larger particle size of the drug coated on the surface of the DESs, an optimum diffusion of the drug into the tissues of an artery is not achieved. The diffusion of the drug into the tissues of the artery further depends on properties of the drug. For example, sirolimus eluting stents exhibit a poor diffusion of sirolimus into the tissues of the artery because of low solubility associated with sirolimus. Therefore, sirolimus eluting stents may exhibit focal restenosis that is as high as 71% of the total restenosis. Whereas, paclitaxel eluting stents may exhibit focal restenosis that is as high as 56% of the total restenosis. Additionally, most of the drugs that are administered to a patient using the current DESs are hydrophobic in nature and have less affinity for body tissues. As a result, a high amount of the drug needs to be loaded in the DESs for achieving the desired therapeutic effect.

Therefore, there is a need in the art for an improved drug-delivering insertable medical device associated with reduced instances of focal restenosis, edge restenosis, total restenosis, acute thrombus formation, sub-acute thrombus formation, late thrombus formation, delayed healing of lesions, and improper healing of lesions. Further, an improved drug-delivering insertable medical device is needed in the art that may reduce the duration of anti-platelet therapy otherwise advised to patients with the delayed healing of lesions and/or the improper healing of lesions post deployment of the DES. In addition, an improved drug releasing medical device that provides for enhanced bioavailability of the drugs, enhanced biocompatibility and delivery of a drug to maximum portion of a lesion in the blood vessel with optimum drug loading is also needed in the art.

DETAILED DESCRIPTION OF THE INVENTION

Before describing in detail embodiments that are in accordance with the invention, it should be observed that the embodiments reside primarily in combinations of components of a medical device for treating a medical condition associated with a body lumen. Accordingly, the components have been described to include only those specific details that are pertinent to understanding the embodiments of the invention so as not to obscure the disclosure with details that will be readily apparent to those of ordinary skill in the art having the benefit of the description herein.

In this document, the terms "comprises", "comprising" or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Further, before describing in detail embodiments that are in accordance with the invention, it should be observed that all the scientific and technical terms used herein for describing the invention have same meanings as would be understood by a person skilled in the art.

In addition, before describing in detail embodiments that are in accordance with the invention, it should be observed that a drug-delivering insertable medical device may be a medical device that may be inserted or implanted in a body lumen for delivering a drug to a target site in the body lumen. The drug-delivering insertable medical device may be one of, for example, a stent, a balloon, a stent mounted on a balloon (a pre-crimped stent) and a balloon catheter. The drug-delivering insertable medical device may be any other medical device used for performing percutaneous transluminal angioplasty procedures that may deliver nano-carriers of the drug to the target site without departing from the scope of the invention.

The stent may be one of, for example, an endovascular stent, a peripheral vascular stent, a urethral stent, a prostatic stent, a stent graft, a permanently implantable stent, a temporarily implantable stent, and a stent made up of, one or more of one or more of, but not limited to, a metal, an alloy, a biodegradable polymer, and a non-degradable polymer, SS316L, L605 cobalt-chromium alloy, and nickel-titanium alloy, and any stent that may be coated with the nano-carriers of the drug. Additionally, the stent may be any stent coated with one or more of, but not limited to, a biodegradable polymer, a biocompatible polymer a bioerodable polymer and a non-degradable polymer.

The balloon may be any balloon made up of an elastomeric material that may be inflated using suitable inflating means in the percutaneous transluminal angioplasty procedures and that may be coated with the nano-carriers of the drug for delivering the two or more nano-carriers to the target site in the body lumen. The balloon may be one of, for example, an angioplasty balloon and any other balloon used for interventional cardiovascular procedures.

The pre-crimped stent may be a stent mounted on a balloon such that the pre-crimped stent may be coated with the nano-carriers of the drug when the stent is mounted on the balloon. The pre-crimped stent may further include two or more of, the balloon, the stent mounted on the balloon, a shaft and a hypotube.

Further, the drug-delivering insertable medical device may one of, for example, a spinal implant, a percutaneous implant, a transdermal drug delivery device, a dental implant, any surgical implant, and a medical device that may be inserted into a human body for delivery of one or more drugs at a particular site in a human body.

It should be observed that, hereinafter, the nano-carriers of the drug may also be referred to as one or more of, nano-carriers, a first set of nano-carriers, a second set of nano-carriers, a third set of nano-carriers and two or more nano-carriers.

Generally speaking, pursuant to various embodiments, a drug-delivering insertable medical device for treating a medical condition associated with a body lumen is disclosed. The medical condition may be one of, restenosis, blocked body lumen, atherosclerosis, myocardial infarction and plaque accumulation in the body lumen. The body lumen can be for example, a blood vessel a urethra, an esophagus, a ureter and a bile duct.

The drug-delivering insertable medical device includes an outer surface coated with two or more nano-carries. The outer surface of the drug-delivering insertable medical device comes in direct contact with a target site in the body lumen when the drug-delivering insertable medical device is inflated or expanded upon positioning at the target site. A nano-carrier of the two or more nano-carriers includes a drug surrounded by an encapsulating medium. As the drug is surrounded by the encapsulating medium, the surface of the nano-carriers is devoid of the drug. The encapsulating medium includes one or more of a biological agent, a blood excipient and a phospholipid. The two or more nano-carriers have two or more average diameters. The nano-carrier of the two or more nano-carriers has an average diameter suitable for penetrating one or more layers of two or more layers of the body lumen. When the drug-delivering insertable medical device comes in proximity to a target site in the body lumen, the two or more nano-carriers are released from the outer surface. Thereafter, the nano-carrier of the two or more nano-carriers penetrates the one or more layers of the two or more layers of the body lumen based on the average diameter. Thus, a size-dependent penetration of the nano-carrier across the one or more layers of the two or more layers of the body lumen is achieved.

In an embodiment, the drug-delivering insertable medical device is employed for a treating a medical condition associated with a blood vessel. The blood vessel may be one of, for example, a coronary artery, a peripheral artery, a carotid artery, a renal artery, an illiac artery, arteries below a knee, and a vein. The blood vessel includes two or more layers of the tissues. The two or more layers of the tissues include an intima layer, a media layer and an adventitia layer. The intima layer includes an innermost layer of tissues of the blood vessel that is in direct contact with the blood flow through the blood vessel. The media layer includes a layer of tissues of the blood vessel that is beneath the intima layer. Whereas, the adventitia layer includes a layer of tissues of the blood vessel that is beneath the media layer.

The outer surface of drug-delivering insertable medical device is coated with the two or more nano-carriers. In an exemplary embodiment, when a pre-crimped stent is used as the drug-delivering insertable medical device, the outer surface such as one or more portions of an abluminal surface of the pre-crimped stent and one or more portions of the balloon that are exposed through the pre-crimped stent are coated with two or more nano-carriers. According to various embodiments, only the outer surface of the drug-delivering insertable medical device is coated with the two or more nano-carriers. Whereas, the inner surface of the drug-delivering insertable medical device is substantially devoid of the two or more nano-carriers. Accordingly, in an exemplary embodiment, when the drug-delivering insertable medical device is a stent, only the abluminal surface of the stent is coated with the two or more nano-carriers. Whereas, the luminal surface of the stent is substantially devoid of the two or more nano-carriers. Such selective coating of the outer surface may minimize the instances of delayed healing.

Accordingly, when the drug-delivering medical device comes in proximity of the blood vessel, a nano-carrier of the two or more nano-carriers may penetrate one or more of the intima layer, the media layer and the adventitia layer based on an average diameter associated with the nano-carrier. A nano-carrier penetrates one or more of the intima layer, the media layer and the adventitia layer by passing through one or more of inter-tissue pores present in the intima layer, a vasa vasorum associated with the media layer and a vasa vasorum associated with the adventitia layer. The inter-tissue pores present in the intima layer, the vasa vasorum associated with the media layer and the vasa vasorum associated with the adventitia layer have different internal diameters. Therefore, penetration of the nano-carrier of the two or more nano-carriers into one or more of the intima layer, the media layer and the adventitia layer depends upon the average diameter associated with the nano-carrier.

The two or more nano-carriers coated on the outer surface of the drug-delivering medical device have two or more average diameters. The two or more average diameters may range from 1 nm to 5000 nm.

In an embodiment, the drug-delivering medical device may be coated with a first set of nano-carriers, a second set of nano-carriers, and a third set of nano-carriers. The first set of nano-carriers has a first average diameter suitable for penetrating the intima layer through the inter-tissue pores present in the intima layer. The second set of nano-carriers have a second average diameter suitable for penetrating the media layer through the vasa vasorum associated with the media layer and the inter-tissue pores present in the intima layer. The third set of nano-carriers have a third diameter suitable for penetrating the adventitia layer through the inter-tissue pores present in the intima layer, the vasa vasorum associated with the media layer and the vasa vasorum associated with the adventitia layer.

In an embodiment, the first average diameter may range from 800 nm to 1500 nm, the second average diameter may range from 300 nm to 800 nm and the third average diameter may range from 10 nm to 300 nm. In another embodiment, the first average diameter is 1000 nm, the second average diameter is 700 nm and the third average diameter is 200 nm. The first average diameter, the second average diameter and the third average diameter may be varied to meet a particular therapeutic need without departing from the scope of the invention.

The two or more nano-carriers coated on the drug-delivering medical device may include 10% to 60% of the first set of nano-carriers, 20% to 60% of the second set of nano-carriers and 30% to 80% of the third set of nano-carriers. Alternatively, the two or more nano-carriers may be coated to include about 15% to 90% of the first set of nano-carriers, 10% to 85% of the second set of nano-carriers and 5% to 85% of the third set of nano-carriers.

Accordingly, when the drug-delivering medical device comes in proximity to the target site in the blood vessel, the two or more nano-carriers corresponding to one or more of the first set of nano-carriers, the second set of nano-carriers, and the third set of nano-carriers are released from the outer surface of the drug-delivering insertable medical device. Subsequently, the two or more nano-carriers thus released penetrate the one or more layers of the blood vessel based on respective average diameters associated with the two or more nano-carriers. Thus, a size dependent penetration of the two or more nano-carriers is achieved.

In addition to the size dependent penetration of the two or more nano-carriers, a rate at which a nano-carrier is released from the outer surface of the drug-delivering medical device is also controlled with the help of an average diameter of the nano-carrier. A nano-carrier with a small average diameter is rapidly released by the drug-delivering medical device. Therefore, time required for the third set of nano-carriers to release from the outer surface upon coming in proximity of the target site is less than the time required for the second set of nano-carriers and the first set of nano-carriers to get released from the outer surface. Thus, the third set of nano-carriers exhibit a rapid rate of release from the outer surface. Whereas, the second set of nano-carriers and the third set of nano-carriers exhibit slower rates of release from the outer surface as compared with the rate of release of the third set of nano-carriers.

Once the two or more nano-carriers are released and are penetrated across the one or more layers of the blood vessel, the drug is released from the two or more nano-carrier into one or more of the adventitia layer, the media layer and the intima layer. The drug is released when the encapsulating medium is dissolved. Thus, an in-tissue release of the drug at the target site is achieved. Further, one or more nano-carriers that penetrate into the adventitia layer may remain in the adventitia layer for a prolonged time. In other words, the adventitia layer may act as a reservoir of the drug from where the drug is slowly released over the prolonged time.

Additionally, the drug may further diffuse across the one or more of the adventitia layer, the media layer and the intima layer during the prolonged time. In such an instance, the drug that is diffused across the one or more of the adventitia layer, the media layer and the intima layer may provide an in-tissue diffusion of the drug for the prolonged time. Thus, because of the in-tissue release of the drug and in-tissue diffusion of the drug, a maximum portion of lesions at the target site is supplied with the drug. Therefore, the probable chances of focal restenosis are reduced as compared with the conventional DESs.

In addition, because of the in-tissue release of the drug and the in-tissue diffusion of the drug for the prolonged time, the instances of delayed healing and improper healing of the lesions at the target site are minimized as compared with the conventional DESs. As a result, an anti-platelet therapy that has to be given to the patients with delayed healing and/or improper healing of the lesions may also be minimized.

Further, as the encapsulating medium includes one or more of a biological agent, a blood excipient and a phospholipid, the two or more nano-carriers exhibit an affinity for the tissues of the target site. Such an affinity facilitates efficient transferring of the two or more nano-carriers from the outer surface of the drug-delivering insertable medical device to the target site over a time. As a result, substantially each of the first set of nano-carriers, the second set of nano-carriers, and the third set of nano-carriers are released from the outer surface over the time. Thereafter, the outer surface of the drug-delivering insertable medical device may become substantially devoid of the two or more nano-carriers over the time. In an exemplary embodiment, where the drug-delivering insertable device is a stent, the stent may become substantially devoid of the two or more nano-carriers within 7 to 45 days after deployment of the stent at the target site. In another exemplary embodiment, the stent may become substantially devoid of the two or more nano-carriers within about 30 days of deployment of the stent.

In addition, the encapsulating medium also keeps the surface of the nano-carrier devoid of any free drug. This facilitates in avoiding a direct contact of the drug with the surface of the drug-delivering insertable medical device. Further, the drug comes in contact with the tissues of the target site only when the nano-carrier penetrates into the one or more layers of the blood vessel and the encapsulating medium is dissolved. Thus, direct exposure of the drug to the tissues of the target site and the surface of the drug-delivering insertable medical device is prevented.

The drug may include nano-crystals of the drug. The nano-crystals of the drug may have an average diameter ranging from 1 nm to 5000 nm. Further, the nano-crystals of the drug may have two or more different average diameters. Alternatively, the drug may be one or more of, nano-sized particles, nano-spheres, liposomes, nano-capsules, dendrimers, and any other similar form of the drug that has nano-dimensions. The drug may be one or more of, but are not limited to, an anti-proliferative agent, an anti-inflammatory agent, an anti-neoplastic agent, an anti-coagulant agent, an anti-fibrin agent, an antithrombotic agent, an anti-mitotic agent, an antibiotic agent, an anti-allergic agent and an antioxidant, an anti-proliferative agent, estrogens, a protease inhibitor, antibodies, an immunosuppressive agent, a cytostatic agent, a cytotoxic agent, a calcium channel blocker, a phosphodiesterase inhibitor, a prostaglandin inhibitor, a dietary supplement, vitamins, anti-platelet aggregating agent and genetically engineered epithelial cells.

The drug may be one or more of, for example, but are not limited to, sirolimus, paclitaxel, tacrolimus, clobetasol, dexamethasone, genistein, heparin, 17 beta-estadiol, rapamycin, everolimus, ethylrapamycin, zotarolimus, ABT-578, Biolimus A9, docetaxel, methotrexate, azathioprine, vincristine, vinblastine, fluorouracil, doxorubicin hydrochloride, mitomycin and analogs thereof, miomycine, sodium heparin, a low molecular weight heparin, a heparinoid, hirudin, argatroban, forskolin, vapiprost, prostacyclin, a prostacyclin analogue, dextran, D-phe-pro-arg-chloromethylketone, dipyridamole, glycoprotein IIb/IIIa, recombinant hirudin, bivalirudin, nifedipine, colchicines, lovastatin, nitroprusside, suramin, a serotonin blocker, a steroid, a thioprotease inhibitor, triazolopyrimidine, a nitric oxide or nitric oxide donor, a super oxide dismutase, a super oxide dismutase mimetic, estradiol, aspirin, angiopeptin, captopril, cilazapril, lisinopril, permirolast potassium, alpha-interferon, bioactive RGD and any salts or analogues thereof.

The drug is surrounded by the encapsulating medium. The encapsulating medium may be one or more of, a biological agent, a blood excipient and a phospholipid. Alternatively, the encapsulating medium may be one or more of, one or more biological agents, one or more blood excipients, one or more phospholipids and one or more excipients. The biological agent may include nano-particles of the biological agent. The nano-particles of the biological agent may have an average diameter ranging from 1 nm to 5000 nm. Further, the nano-particles of the biological agent may have two or more different average diameters. Alternatively, the biological agent may include one or more of, nano-sized particles, nano-spheres, liposomes, nano-capsules, dendrimers, and any other similar form of the biological agent that has nano-dimensions.

The biological agent may be one or more of, but are not limited to, drug carriers, excipients, blood components, excipients derived from blood, naturally occurring phospholipids, solid lipid nano-particles, phospholipids obtained from a living animal, synthetically derived phospholipids, lipoids, vitamins and sugar molecules. The biological agent may be, for example, but are not limited to, steroids, vitamins, estradiol, esterified fatty acids, non esterified fatty acids, glucose, inositol, L-lactate, lipoproteins, carbohydrates, tricalcium phosphate, precipitated calcium phosphate, calcium phoshate tribasic, substances derived from at least one of human, egg and soybean, phospholipon 80H, phospholipon 90H, Lipoids S75, Lipoids E80, Intralipid 20, Lipoid EPC, Lipoid E75, lipids obtained from egg, lipids obtained from soya, phosphatidylcholine, phosphatidylglycerol, phosphatidylinositol, phosphatidylserine, phosphatidic acid, cardiolipin, and phosphatidylethanolamine.

The phospholipid may include nano-particles of the phospholipid. The nano-particles of the phospholipid may have an average diameter ranging from 1 nm to 5000 nm. Further, the nano-particles of the phospholipid may have two or more different average diameters. Alternatively, the phospholipid may include one or more of, nano-sized particles, nano-spheres, liposomes, nano-capsules, dendrimers, and any other similar form of the phospholipid that has nano-dimensions. The phospholipid may include one or more of, but are not limited to, lipids obtained from egg, lipids obtained from soya, phosphatidylcholine, phosphatidylglycerol, phosphatidylinositol, phosphatidylserine, phosphatidic acid, cardiolipin, and phosphatidylethanolamine.

The blood excipient may include nano-particles of the blood excipient. The nano-particles of the blood excipient may have an average diameter ranging from 1 nm to 5000 nm. Further, the nano-particles of the blood excipient may have two or more different average diameters. Alternatively, the blood excipient may include one or more of, nano-sized particles, nano-spheres, liposomes, nano-capsules, dendrimers, and any other similar form of the blood excipient that has nano-dimensions. The blood excipient may be one or more of, but are not limited to, steroids, vitamins, estradiol, esterified fatty acids, non-esterified fatty acids, glucose, inositol, L-lactate, lipids, lipoproteins, phospholipid, carbohydrates, tricalcium phosphate, precipitated calcium phosphate, and calcium phoshate tribasic.

The blood excipient and the biological agent are soluble at a pH below 7.4. Therefore, when the two or more nano-carriers come in contact with the tissues of the target site, the biological agent and the blood excipient get dissolved in the blood. The dissolution of the biological agent and the blood excipient results in the release of the drug from the two or more nano-carriers at the target site. Thus, a pH dependent release of the drug from the two or more nano-carriers is achieved.

In an exemplary embodiment, the drug-delivering insertable medical device is a coronary stent. The coronary stent is, for example, Chromium Cobalt L-605 stent. The coronary stent includes an abluminal (outer) surface coated with the two or more nano-carriers. The two or more nano-carriers include a first set of nano-carriers with an average diameter of about 1200 nm, the second set of nano-carriers with an average diameter of about 700 nm and the third set of nano-carriers with an average diameter of about 200 nm. When the stent comes in proximity of the target site the two or more nano-carriers are released from the abluminal surface of the stent. Thereafter, the first set of nano-carriers penetrates the intima layer through the inter-tissue pores present in the intima layer. The second set of nano-carriers penetrate the media layer through the vasa vasorum associated with the media layer and the inter-tissue pores present in the intima layer. The third set of nano-carriers penetrate the adventitia through the vasa vasorum associated with the adventitia layer, the vasa vasorum associated with the media layer and the inter-tissue pores present in the intima layer.

In another exemplary embodiment, the drug-delivering insertable medical device is a balloon. The balloon is, for example, an ultrathin angioplasty balloon. The balloon includes an outer surface coated with the two or more nano-carriers. The two or more nano-carriers include a first set of nano-carriers with an average diameter of about 1200 nm, the second set of nano-carriers with an average diameter of about 700 nm and the third set of nano-carriers with an average diameter of about 200 nm. When the balloon is inflated upon coming in proximity of the target site the two or more nano-carriers are released from the abluminal surface of the stent. Thereafter, the first set of nano-carriers penetrates the intima layer through the inter-tissue pores present in the intima layer. The second set of nano-carriers penetrates the media layer through the vasa vasorum associated with the media layer and the inter-tissue pores present in the intima layer. The third set of nano-carriers penetrates the adventitia through the vasa vasorum associated with the adventitia layer, the vasa vasorum associated with the media layer and the inter-tissue pores present in the intima layer. The balloon may be coated with the two or more nano-carriers when the balloon is in a folded configuration or an unfolded configuration.

In yet another exemplary embodiment, the drug-delivering insertable medical device is a pre-crimped stent (a stent mounted on a balloon). For example, the pre-crimped stent is a Chromium Cobalt L-605 stent mounted on an ultrathin angioplasty balloon. The pre-crimped stent is coated with the two or more nano-carriers. A nano-carrier of the two or more nano-carriers coated on the pre-crimped stent includes nano-crystals of sirolimus encapsulated with nano-particles of one or more of soya phospholipid and tricalcium phosphate. The two or more nano-carriers include a first set of nano-carriers with average diameter of 1200 nm, a second set of nano-carriers with average diameter of 700 nm and a third set of nano-carriers with average diameter of 200 nm.

An outer surface of the pre-crimped stent is coated with the two or more nano-carriers when the stent is mounted on the balloon. One or more portions of the balloon that are not covered by the stent (one or more portions of the balloon that are exposed through one or more struts of the sent) are also coated with the two or more nano-carriers along with the abluminal surface of the stent. As the luminal surface of the stent is covered by the balloon, only the abluminal surface of the stent is coated with the two or more nano-carriers. When the pre-crimped stent comes in proximity to the target site, the balloon is inflated. The inflation of the balloon causes an expansion of the stent. In response to the inflation of the balloon and the expansion of the stent at the target site in the coronary artery, the two or more nano-carriers are released from the pre-coated stent. The two or more nano-carriers coated on the one or more portions of the balloon provide for a burst release of the one or more nano-carriers from the balloon. Whereas, the two or more nano-carriers coated on the abluminal surface of the stent provide for controlled release of the two or more nano-carriers from the abluminal surface of the stent.

Additionally, the outer surface of the pre-crimped stent may include a portion of the balloon that extends longitudinally beyond one or more of a distal boundary and a proximal boundary of the stent. In such a case, a portion that longitudinally extends at least 0.05 mm beyond one or more of the distal boundary of the stent and the proximal boundary of the stent may also be coated with the two or more nano-carriers. Coating the portion that longitudinally extends at least 0.05 mm beyond the distal boundary of the stent or/and the proximal boundary of the stent with the two or more nano-carriers, provides for delivery of the drug to the lesions present beyond the distal boundary and/or proximal boundary of the stent. Thus, probable chances of edge restenosis following deployment of the stent in a subject may be minimized.

In still yet another exemplary embodiment, a pre-crimped stent (a stent mounted on a balloon) is coated with two or more layers of the two or more nano-carriers. An outer layer of the two or more layers coated on the balloon and the stent includes the third set of nano-carriers. Whereas, an inner layer of the two or more layers coated on the balloon and the stent includes one or more of the first set of nano-carriers and the second set of nano-carriers. The third set of nano-carriers present in the outer layer on the balloon and the stent provide for burst release of the third set of nano-carriers when the pre-crimped stent comes in proximity to the target site. Whereas, the one or more of the second set of nano-carriers and the first set of nano-carriers present in the inner layer provide for a controlled release of the one or more of the second set of nano-carriers and the first set of nano-carriers from the pre-crimped stent.

In an embodiment, the drug-delivering insertable medical device includes an outer surface coated with two or more layers of the two or more nano-carriers. The two or more nano-carriers present in an outer layer of the two or more layers include a first set of drugs. Whereas, two or more nano-carriers present in an inner layer of the two or more layers include a second set of drugs. The second set of drugs may include one or more drugs that are different from one or more drugs present in the first set of drugs. The first set of drugs may include for example, but not limited to, one or more of an anti-inflammatory agent and an anti-thrombotic agent. The first set of drugs being present in the outer layer will provide for burst release. Thus, first set of drugs may be delivered to the target site to control the inflammation or injury that may be caused by the drug-delivering insertable medical device. Whereas, the second set of drugs may include for example, but not limited to, an anti-proliferative agent. The second set of the drugs that is present in the inner layer is released from the outer surface after the outer layer is released. Thus, the second set of drugs may be delivered over a period of time to control the proliferative phase of the inflammation cell cycle.

One or more of the first set of drugs and the second set of drugs may be selected from one or more of, but are not limited to, an anti-neoplastic agent, an anti-coagulant agent, an anti-fibrin agent, an antithrombotic agent, an anti-mitotic agent, an antibiotic agent, an anti-allergic agent and an antioxidant, estrogens, a protease inhibitor, antibodies, an immunosuppressive agent, a cytostatic agent, a cytotoxic agent, a calcium channel blocker, a phosphodiesterase inhibitor, a prostaglandin inhibitor, a dietary supplement, vitamins, anti-platelet aggregating agent and genetically engineered epithelial cells without departing from the scope of the invention.

In another embodiment, the drug-delivering insertable medical device is coated with three layers of the two or more nano-carriers. An inner-most layer of the three layers of the two or more nano-carriers includes a prohealing agent. A middle layer of the three layers includes an anti-proliferative agent and an outer-most layer of the three layers includes one or more of an anti-inflammatory agent and an anti-thrombogenic agent. The outer-most layer provides for burst release of the two or more nano-carriers. Thus, the outer-most layer that contains one or more of the anti-inflammatory agent and the anti-thrombogenic agent may address the inflammation. The middle layer that contains the anti-proliferative agent releases the two or more nano-carriers after the two or more nano-carriers of the outer-most layer are released. Thus, the middle layer may address the proliferative phase of the inflammation cell cycle at the target site. Whereas, the inner-most layer releases the two or more nano-carriers after the two or more nano-carriers of the middle layer are released. Thus, the inner-most layer that contains the prohealing agent may be helpful in promoting extracellular matrix formation at the target site thereby addressing the regeneration phase of the inflammation cell cycle. Thus, the drug-delivering insertable medical device may be designed to address the various phases of the inflammation cell cycle at the target site.

Generally speaking, pursuant to various embodiments, the invention also discloses a method for treating a medical condition associated with a body lumen. The medical condition may be one of, restenosis, blocked body lumen, atherosclerosis, myocardial infarction and plaque accumulation in the body lumen. The body lumen may be, for example, a blood vessel, a urethra, an esophagus, a ureter and a bile duct. In an embodiment, the method includes delivering two or more nano-carriers to a target site in the blood vessel by using a drug-delivering insertable medical device having an outer surface coated with two or more nano-carriers.

The method further includes positioning the drug-delivering insertable medical device at a target site in the blood vessel. Thereafter, the drug-delivering insertable medical device is expanded or inflated. In response to expanding or inflating the drug-delivering insertable medical device, the outer surface of the drug-delivering insertable medical device comes in contact with the target site and the two or more nano-carriers are released from the outer surface. The two or more nano-carriers thus released then penetrate one or more of the two or more layers of the blood vessel depending upon respective average diameters associated with the two or more nano-carriers.

A nano-carrier of the two or more nano-carriers includes a drug surrounded by an encapsulating medium. The encapsulating medium includes one or more of a biological agent, a blood excipient and a phospholipid. In accordance with various embodiments, the drug may include nano-crystals of the drug. Whereas, the biological agent, the phospholipid and the blood excipient may include nano-particles of the biological agent, the phospholipid and the blood excipient, respectively. The nano-crystals of the drug, the nano-particles of the biological agent, the nano-particles of the phospholipid and the nano-particles of the blood excipient may be obtained by conventional methods. Alternatively, the nano-crystals of the drug, nano-particles of the biological agent, the nano-particles of the phospholipid and the nano-particles of the blood excipient available in the market may also be used. For example, one or more of the nano-crystals of the drug, the nano-particles of the biological agent, the nano-particles of the phospholipid and the nano-particles of the blood excipient may be obtained by using one or more of, but are not limited to, high-pressure homogenization, spray drying, high speed homogenization, ball milling, pulverization, sol-gel methods, hydrothermal methods, spray pyrolysis method and the like.

A nano-carrier is obtained by encapsulating the nano-crystals of the drug by the nano-particles of one or more of the biological agent, the phospholipid, and the blood excipient by using methods known in the art. The nano-carrier thus obtained may have an average diameter ranging from 1 nm to 5000 nm.

In an embodiment, a first set of the nano-crystals of the drug with an average diameter of 1200 nm, a second set of the nano-crystals of the drug with an average diameter of 700 nm and third set of the nano-crystals of the drug with an average diameter of 200 nm are obtained using one or more methods known in the art. Further, a first set of the nano-particles of the biological agent with an average diameter of 1200 nm, the second set of the nano-particles of the biological agent with an average diameter of 700 nm and the third set of the nano-particles of the biological agent with an average diameter of 200 nm are obtained using one or more methods known in the art.

Thereafter, a solution of the first set of the nano-crystals of the drug, a solution of second set of the nano-crystals of the drug and a solution of the third set of the nano-crystals of the drug are obtained by using a suitable solvent. Similarly, a solution of the first set of the nano-particles of the biological agent, a solution of second set of the nano-particles of the biological agent and a solution of the third set of the nano-particles of the biological agent are obtained by using a suitable solvent.

Subsequently, the solution of the first set of nano-crystals of the drug and the solution of the first set of the nano-particles of the biological agent are subjected to an encapsulation process to obtain a first set of nano-carriers with a first average diameter. Similarly, the solution of the second set of nano-crystals of the drug and the solution of the second set of the nano-particles of the biological agent are subjected to an encapsulation process to obtain a second set of nano-carriers with a second average diameter. Whereas, the solution of the third set of nano-crystals of the drug and the solution of the third set of the nano-particles of the biological agent are subjected to an encapsulation process to obtain a third set of nano-carriers with a third average diameter.

The first set of nano-carriers, the second set of nano-carriers and the third set of nano-carriers thus obtained are then coated as one or more layers on an outer surface of the drug-delivering insertable medical device using the methods known in the art.

In an exemplary embodiment, a solution of the first set of the nano-carriers, a solution of the second set of the nano-carriers and the third set of the nano-carriers may be obtained using a suitable solvent. Thereafter, the solution of the first set of the nano-carriers, the solution of the second set of the nano-carriers and the solution of the third set of the nano-carriers may be coated on the outer surface of the drug-delivering insertable medical device using a coating machine known in the art.

The coating machine may have a rotatable mandrel. The drug-delivering insertable medical device may be mounted on the rotatable mandrel and rotated along with the rotatable mandrel. The outer surface of the drug-delivering insertable medical device may be exposed to the atomization nozzle. Thereafter, one or more of the solution of the first set of the nano-carriers, the solution of the second set of the nano-carriers and the solution of the third set of the nano-carriers may be sprayed on the outer surface to obtain the drug-delivering insertable medical device coated with one or more of the first set of nano-carriers, the second set of nano-carriers and third set of nano-carriers.

The coating machine may have one or more reservoirs for storing the solution of the first set of the nano-carriers, the solution of the second set of the nano-carriers and the solution of the third set of the nano-carriers. For example, the solution of the first set of the nano-carriers, the solution of the second set of the nano-carriers and the solution of the third set of the nano-carriers may be stored in three different reservoirs.

Alternatively, the solution of the first set of the nano-carriers, the solution of the second set of the nano-carriers and the solution of the third set of the nano-carriers may be stored as a mixture in a single reservoir. The one or more reservoirs may supply one or more of the solution of the first set of the nano-carriers, the solution of the second set of the nano-carriers and the solution of the third set of the nano-carriers to an atomization nozzle. The atomization nozzle may be used to spray the solution of the first set of the nano-carriers, the solution of the second set of the nano-carriers and the solution of the third set of the nano-carriers on the surface of the drug-delivering insertable medical device.

In another embodiment, the two or more nano-carriers are coated as two layers on the outer surface of the drug-delivering insertable medical device. The drug-delivering insertable medical device is prepared by spraying, for example, the solution of the third set of the nano-carriers on the outer surface. Subsequently, the drug-delivering insertable medical device may be dried. Thereafter, one or more of the solution of the second set of the nano-carriers and the solution of the first set of the nano-carriers may be sprayed on the outer surface. Subsequently, the drug-delivering insertable medical device may be dried. Thus, the drug-delivering insertable medical device with two layers of the two or more nano-carriers may be obtained.

Thereafter, the drug-delivering insertable medical device coated with two or more nano-carriers is inserted into the blood vessel using a catheter assembly. The catheter assembly may include a guide wire, a catheter, a balloon, a stent mounted on the balloon and an inflation mechanism for inflating the balloon. The guide wire is advanced in the blood vessel to pass just a small distance beyond the target site. The catheter with the stent and the balloon mounted on a distal end of the catheter is then advanced over the guide wire in such a way that the stent mounted on the balloon is positioned at the target site. Once the stent mounted on the balloon reaches the target site in the blood vessel, the balloon is inflated using the inflation mechanism. Upon inflation of the balloon, the stent mounted on the balloon also expands and an outer surface of the stent and a portion of the balloon exposed through the stent come in contact with a wall of the blood vessel at the target site. When the balloon comes in contact with the target site, the two or more nano-carriers coated on the balloon are released from the balloon and get delivered to the target site. Thereafter, the balloon is deflated and withdrawn from the blood vessel, leaving the stent at the target site. The stent at the target site may release the two or more nano-carriers at the target site in the blood vessel over a prolonged time. The two or more nano-carriers thus released then penetrate one or more of the two or more layers of the blood vessel depending upon their respective average diameters associated.

In instances, the medical device may include a stent mounted on a balloon. The stent mounted on the balloon may be exposed to the atomization nozzle and may be sprayed with the solution of the two or more nano-carriers. Thus, one or more portions of the balloon that is not covered by the stent (one or more portions of the balloon exposed through the struts of the stent) are also coated with the two or more nano-carriers. The one or more portions of the balloon that are coated with the two or more nano-carriers provides for rapid release of the two or more nano-carriers from the drug-delivering insertable medical device to the target site. Whereas, the two or more nano-carriers that are coated on the outer surface of the stent provide for delayed release of the two or more nano-carriers from the outer surface of the drug-delivering insertable medical device to the target site.

Example 1

Soya phospholipid was obtained from Lioid GMBH, Batch No.: 776114-1/906. Sirolimus was obtained from Fujan Chemicals, China with purity greater than 99.5%. The water, other solvents and reagents used were of HPLC grade. Amazonia Croco® (Chromium cobalt coronary L-605 stent system mounted on ultrathin angioplasty balloon, hereinafter "the stent system") was obtained from Minvasys, Paris, France.

Figure 1:
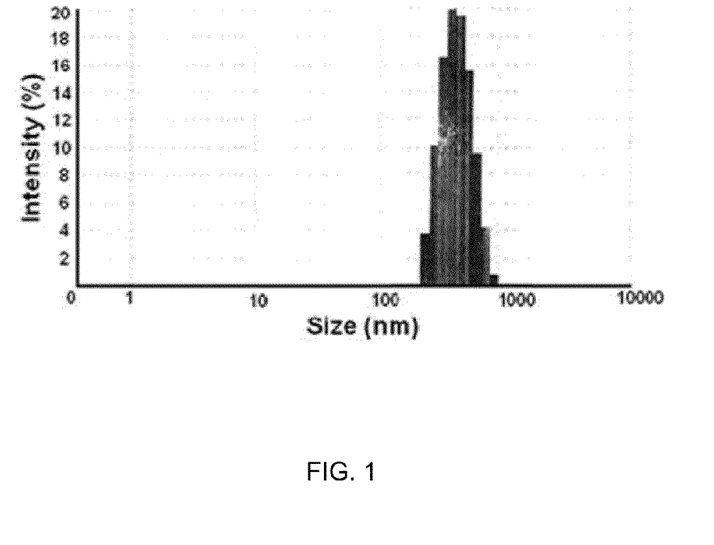
FIG. 1 illustrates the size distribution of nano-particles of soya phospholipid as detected by Malvern ZS90 in accordance with Example 1.

Soya phospholipid (20 mg w/w) was added to de-ionized water (10 ml) followed by Tween 80 (5 mg) to obtain aqueous solution of soya phospholipid. The aqueous solution of soya phospholipid (10 ml) was subjected to a high speed homogenization at 15000-20000 rpm for 20 to 25 minutes in ice-cold water bath to obtain Solution A1. The Solution A1 thus obtained contained nano-particles of soya phospholipid. The solution A1 was subsequently analyzed for particle size detection using Malvern ZS90 (Malvern, UK) size detector. FIG. 1 illustrates the size distribution of nano-particles of soya phospholipid as detected by Malvern ZS90. The average diameter of the nano-particles of the soya phospholipid was found to be 475.79 nm.

Sirolimus (20 mg w/w) was added to 10 ml of de-ionized water to obtain aqueous solution of sirolimus. The aqueous solution of sirolimus (10 ml) was subjected to a high speed homogenization at 15000-20000 rpm for 150 to 200 minutes in ice-cold water bath to obtain Solution A2. The Solution A2 thus obtained contained nano-crystals of sirolimus. The solution A2 was subsequently analyzed for particle size detection using Malvern ZS90 (Malvern, UK) size detector.

Figure 2:
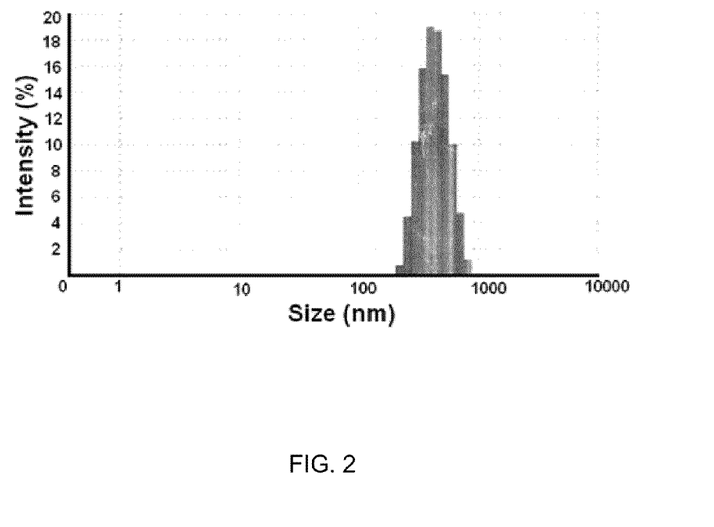
FIG. 2 illustrates the size distribution of nano-carriers as detected by Malvern ZS90 in accordance with Example 1.

Solution A1 was gradually (drop by drop) added to Solution A2 and was subjected to a high speed homogenization at 15000-20000 rpm for 20 minutes to obtain 20 ml Solution A3. Solution A3 was again homogenized for 10 minutes. Solution A3 was then stirred with a magnetic stirrer (2MLH hot plate heater cum stirrer, Accumax, INDIA) for 20 minutes. Solution A3 thus obtained contained nano-carriers (nano-crystals of sirolimus surrounded by nano-particles of soya phospholipid). Solution A3 was subsequently analyzed for particle size detection using Malvern ZS90 (Malvern, UK) size detector. FIG. 2 illustrates the size distribution of nano-carriers as detected by Malvern ZS90. The average particle size was found to be 410 nm.

Solution A3 (Aqueous solution of nano-carriers) was further subjected to extraction with dichloromethane. Solution A3 (20 ml) was transferred to 100 ml separating funnel. 50 ml of dichloromethane was added to the 100 ml separating funnel. The resultant mixture was shaken for 15 min and then allowed to stand. Thereafter, two layers i.e. aqueous layer and the dichloromethane layer were observed in the 100 ml separating funnel. The dichloromethane layer was separated from the aqueous layer. The dichloromethane layer i.e. solution of the nano-carriers was stored in amber colored small measuring flask with batch number. Subsequently, the solution of the nano-carriers was used for coating the stent system.

The solution of the nano-carriers (5 ml) was fed into the reservoir of a coating machine. The stent system was mounted on a rotating mandrel of the coating machine. The stent system was exposed to the atomization nozzle of the coating machine. The stent system was rotated at 5 to 40 rpm by rotating the mandrel and simultaneously the solution of nano-carriers was sprayed over the stent system at 0.5-4.0 psi inert gas pressure and 2 oscillations. Thus the stent system coated with the nano-carriers (hereinafter "the coated stent system") was obtained. The stent system was removed and checked under high resolution microscope for the coating surface smoothness and any foreign particles. The coated stent system was then subjected to further analysis as explained in Example 2 below.

Example 2

Detection of Drug Content of the Stent System:

The amount of sirolimus loaded on the coated stent system was calculated using HPLC analysis. The HPLC operating parameters were selected as: Flow Rate was set at 1.2 ml/min. (±0.01), λ Maxima was set at 278 nm (±1 nm), Column Temperature was set at 60° C. (±2° C.), Sensitivity of detector was set at 0.02 AUFS and Analysis Time was set up to 20 minutes.

HPLC System [LC-10ATVP pump (SHIMADZU, JAPAN)] attached with UV-VIS Detector [SPD-10AVP (SHIMADZU, JAPAN)] and Rheodyne integrator [Analytical Technologies, Analytical 2010] was used for the HPLC analysis. Column-$C_{18}$ [$RP_{18}$ Length 4.6 mm×250 mm, particle size 5 μm] was attached with column oven [PCI] for the heating. 25 μl Hamilton Micro-syringe was used for injecting the samples. The samples were filtered through the millipore PTFE 0.45-micron syringe filter before analysis to avoid any particulate matters. Pre-calibrated class A grade volumetric flasks were used. Amber colored glassware was used to protect against light. All the Renchem solvents and reagents used in the analysis were of HPLC grade. Sirolimus was used as received from Fujan Chemicals, China with purity greater than 99.5%.

Mobile phase included Acetonitrile:Methanol:Water in a concentration ratio of 45:40:15. Mobile phase was subsequently degassed in an ultrasonic cleaner for 10 minutes.

Sirolimus (0.5 mg) was taken in a clean and dry 10 ml Standard Measuring Flask (SMF). The SMF was then filled up to the mark with the mobile phase and shaken for 5 to 10 minutes. The SMF was then kept in an ultrasonic cleaner and degassed for 10 minutes. The solution was then filtered through 0.45 micron syringe filter to obtain the standard solution with "Standard Concentration" of 50 μg/ml.

Figure 3:
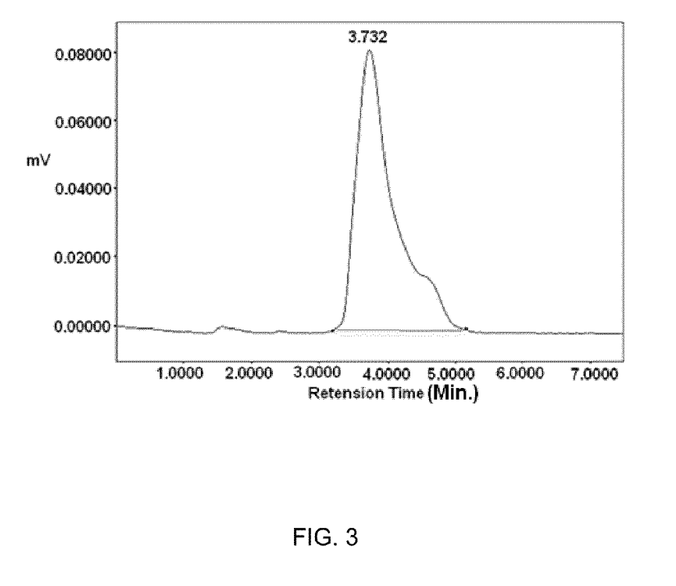
FIG. 3 illustrates a chromatogram for the standard solution in accordance with Example 2.

Using the micro-syringe, 20 μL of the standard solution was injected in the HPLC injector and a chromatogram for the standard solution was obtained. FIG. 3 illustrates a chromatogram for the standard solution. Subsequently, the area of the peak for the standard solution ("Standard Area") was calculated. The retention time for the standard solution was found to be 3.732 minutes and the "Standard Area" corresponding to the peak for the standard solution was found to be 3196.970 mV*Sec.

For the quantification of the drug content loaded on the stent system, the sample solution was prepared by inserting the coated stent system in 10 ml SMF filled with methanol (10 ml). The SMF was then kept in ultrasonic bath for 10 minutes to allow the sirolimus present in the coated stent system to completely dissolve in the methanol. Thus, the sample solution was obtained.

Figure 4:
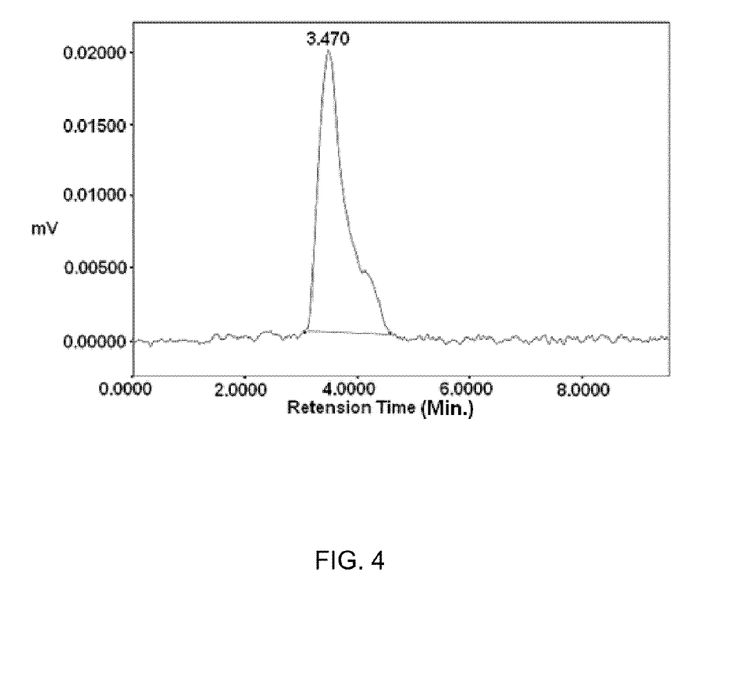
FIG. 4 illustrates a chromatogram for the sample solution the standard solution in accordance with Example 2.

Using the micro-syringe, 20 μL of the sample solution was injected in the HPLC injector and a chromatogram for the sample solution was obtained. FIG. 4 illustrates a chromatogram for the sample solution. Subsequently, the area of the peak for the sample solution ("Sample Area") was calculated. The retention time for the sample solution was found to be 3.470 minutes and the "Sample Area" corresponding to the peak for the sample solution was found to be 683.235 mV*Sec.

Subsequently, the amount of sirolimus present in the coated stent system was calculated using the following formula:

$$\text{Amount of Drug} = (\text{Sample Area/Standard Area}) * (\text{Standard Concentration/Sample Concentration})$$

Therefore, Amount of Drug=(683.235/3196.970)*(50/(1/10))=106.82 μg

Thus, the Amount of Drug loaded on the coated stent system was found to be 106.85 μg.

Example 3

Figure 5:
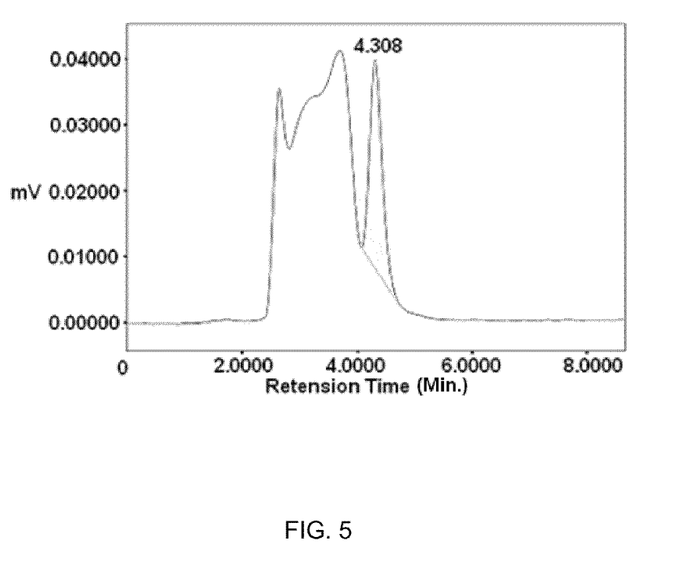
FIG. 5 illustrates a chromatogram for the aqueous solution of nano-carriers in accordance with Example 3.

Encapsulation Efficiency (EE):

1 ml of the aqueous solution of nano-carriers (Example 1) was taken in 10 ml SMF. The volume was adjusted to 10 ml. 20 μL of the aqueous solution of nano-carriers was injected in the HPLC injector and a chromatogram for the aqueous solution of nano-carriers was obtained. FIG. 5 illustrates a chromatogram for the aqueous solution of nano-carriers. The retention time for the aqueous solution of nano-carriers was found to be 4.308 minutes and the "Area for Aqueous Solution of Nano-carriers" corresponding to the peak for the aqueous solution of nano-carriers was found to be 280.555. The amount of free drug was calculated using the following formula:

$$\text{Amount of Free Drug} = (\text{Area for Aqueous Solution of Nano-carriers/Standard Area}) * (\text{Concentration of standard/Concentration of Aqueous Solution of Nano-carriers})$$

Thus, Amount of Free Drug (Sirolimus)=(280.555/3196.970)*(50/(1/10))=43.52. Therefore, the Amount of Free Drug in 1 ml of the Aqueous Solution of Nano-carriers was found to be 43.87 μg. Thus, the Amount of Free Drug present in 20 ml would be 877.4 μg. Subsequently, the % Encapsulation Efficacy was calculated using the following formula:

$$\% \text{ EE} = (\text{Initial Weight of Drug(mg)} - \text{Free Amount of Drug(mg)}) * 100 / (\text{Initial Weight of Drug(mg)})$$

$$\% \text{ EE} = (20 - 0.8774) * 100 / 20 = 95.61\%.$$

Thus, the % encapsulation efficacy was found to be 95.61%.

Example 4

The release of sirolimus from the coated stent system was studied in-vitro by using Phosphate Buffer Saline (PBS) with 6.4 pH. The PBS solution was prepared by dissolving 1.79 g of disodium hydrogen orthophosphate, 1.36 g of potassium hydrogen orthophosphate and 7.02 g of sodium chloride in 1000 ml HPLC grade water. The solution was kept in ultrasonic cleaner for 10 minutes for dissolution.

Three cylindrical vials of 1.5 ml each were filled with freshly prepared PBS. The three vials were designated as, 15 seconds, 60 seconds and Day 1. The 15 seconds vial, 60 seconds vial and Day 1 vial were kept in incubator at 37° C. (±1° C.) for 60 minutes.

The coated sent system was then deepen in the 15 seconds vial and moved up and down for 15 seconds. Thereafter, the coated stent system was transferred to the 60 seconds vial and inflated therein. The inflated stent was kept in the 60 seconds vial for 60 seconds and then was withdrawn from the 60 seconds vial. Subsequently, the coated sent system was then introduced in the Day 1 vial and placed in incubator for 24 hours.

Figure 6:
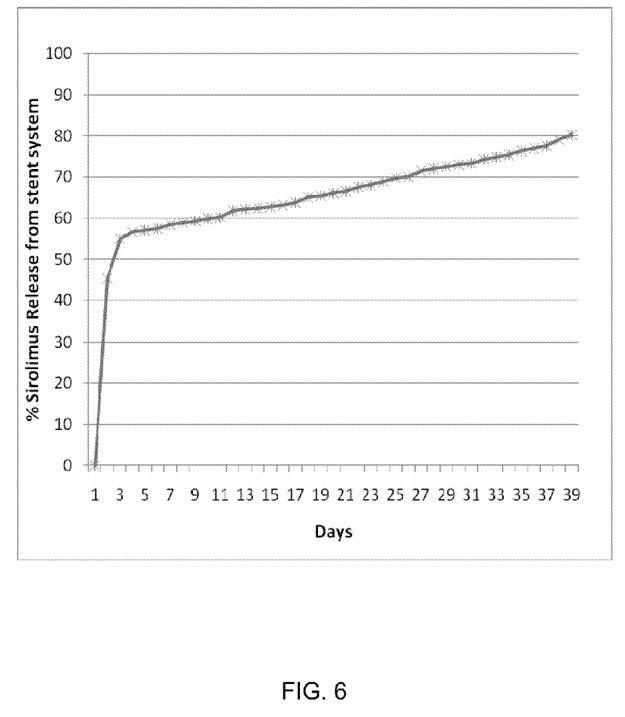
FIG. 6 illustrates the percent sirolimus release from the coated stent system for Day 1 to Day 39, in accordance with Example 4.

The PBS solution from the 15 seconds vial, the 60 seconds vial and the Day 1 vials were transferred to a different separating funnel. Equal amount of methanol (5 ml) was added to all three separating funnels followed by addition of dichloromethane (10 ml). All the three separating funnels were shaken well for 10 minutes and then allowed to stand. Thereafter, the organic phase containing methanol, dichloromethane and sirolimus was separated and subjected to HPLC analysis. Similarly, the coated stent assembly was analyzed for Day 2 to Day 39 by keeping the coated sent assembly for 24 hours each day into a correspondingly marked vial under incubation. The amount of sirolimus present in each vial was determined and the percentage in-vitro release of sirolimus was calculated for Day 1 to Day 39. FIG. 6 illustrates percent sirolimus release from the coated stent system for Day 1 to Day 39. The 15 second vial represented drug lost in transit during angioplasty process. The 60 second vial represented burst release at Day 1 while Day 2 vial to Day 39 vial represented programmed release of sirolimus from the coated stent assembly. It was concluded that by end of Day 39 about 80% of sirolimus was released from the coated stent assembly.

Example 5

Four animals were selected. Each animal of the four animals was implanted with three stents. The three stents included the stent systems (two) and one stent system without sirolimus. QCA results of the implantation and follow-up were analyzed to give the mean luminal diameters of the stented segments prior to the implantation, after the implantation and at 28 days follow-up. The QCA results were used to calculate stent/artery ratio, the acute gain, percent recoil and late loss. The late loss in case of the stent system without sirolimus (BMS) is generally about 1 mm to 1.5 mm. While the late loss in case of the stent systems were found to be 0.45 mm (±0.23 mm). No death associated with the stent systems was reported. Further, thrombosis or restenosis associated with the stent systems was also not reported in any of the four animals. Thus, it was concluded that the stent systems are efficacious and safe as compared with the stent system without sirolimus or the BMSs. In the same study 28 day experiments showed average neointimal thickness of about 150 (±15) microns in the DES and 185 (±50) micron in the excipients coated stents. The qualitative analysis showed complete healing of the neointima in all sirolimus coated stents.

Various embodiments of the invention provide a drug-delivering insertable medical device coated with different average sized nano-carriers of one or more drugs for efficient delivery of the one or more drugs across various layers of a blood vessel. The invention also provides a drug-delivering insertable medical device that exhibits enhanced bioavailability and biocompatibility of the one or more drugs, which in turn results in a small loading dose of the one or more drugs onto the drug-delivering insertable medical device. The drug-delivering insertable medical devices in accordance with the invention is associated with reduced instances of edge restenosis, focal restenosis, total restenosis, sub-acute thrombus formation, late thrombus formation, delayed healing of lesions and improper healing of lesions otherwise associated with the current DESs.

Those skilled in the art will realize that the above-recognized advantages and other advantages described herein are merely exemplary and are not meant to be a complete rendering of all of the advantages of the various embodiments of the invention.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention. The benefits, advantages, solutions to problems, and any element(s) that may cause any benefit, advantage, or solution to occur or become more pronounced are not to be construed as a critical, required, or essential features or elements of any or all the claims. The present invention is defined solely by the appended claims including any amendments made during the pendency of this application and all equivalents of those claims as issued.

What is claimed is:

1. A drug-delivering insertable medical device comprising a stent for treating a medical condition associated with a body lumen comprising an artery, the artery comprising a plurality of layers, the drug-delivering insertable medical device comprising:
    an outer surface coated with a plurality of nano-carriers having a first average diameter, a second average diameter, and a third average diagmeter;
    a nano-carrier of the plurality of nano-carriers comprising a sirolimus drug surrounded by an encapsulating medium, the encapsulating medium comprising at least one of a biological agent, a blood excipient, and a phospholipid, the nano-carrier having an average diameter suitable for penetrating at least one layer of the plurality of layers and a surface of the nano-carrier being devoid of the drug;
    a first set of the nano-carriers having a first average diameter ranging from 800 nm to 1500 nm suitable for penetrating an intima layer of the artery through inter-tissue pores present in the intima layer,
    a second set of nano-carriers having a second average diameter ranging from 300 nm to 800 nm suitable for penetrating a media layer of the artery through a vasa vasorum associated with the media layer and the inter-tissue pores present in the intima layer, and
    a third set of nano-carriers having a third diameter ranging from 10 nm to 300 nm suitable for penetrating an adventitia layer of the artery through the inter-tissue pores present in the intima layer, the vasa vasorum associated with the media layer and a vasa vasorum associated with the adventitia layer;
    wherein the third set of nano-carriers penetrating into the adventitia layer remain in the adventitia layer for a prolonged time and acts as a reservoir of the sirolimus drug to slowly release the sirolimus drug over a prolonged time;
    wherein the sirolimus drug diffuses across the adventitia layer, the media layer and the intima layer during the prolonged time to provide an in-tissue diffusion of the drug for the prolonged time to supply a maximum portion of a lesion of the artery with the sirolimus drug; and
    wherein the prolonged time comprises 39 days.

2. The drug-delivering insertable medical device of claim 1, wherein the at least one of a biological agent and the phospholipid has at least one effect selected from the group consisting of stabilizing the drug, and affinity for the target site.

3. The drug-delivering insertable medical device of claim 1, wherein the drug-delivering insertable medical device is one of a stent or a stent mounted on a balloon.

4. The drug-delivering insertable medical device of claim 3, wherein the drug-delivering insertable medical device is the stent mounted on the balloon, wherein at least a portion of the balloon extending beyond a proximal end of the stent and at least a portion of the balloon extending beyond a distal end of the stent are coated with the plurality of nano-carriers.

5. The drug-delivering insertable medical device of claim 3, wherein the stent and the balloon are coated with at least two layers of the plurality of nano-carriers, wherein an outer layer of the at least two layers corresponding to the balloon and stent comprises at least one nano-carrier with a third average diameter to provide burst release of the at least one nano-carrier with the third average diameter when the balloon is inflated upon coming in proximity with the target site in the body lumen.

6. The drug-delivering insertable medical device of claim 5, wherein the outer layer of the at least two layers corresponding to the stent comprises at least one nano-carrier with the third average diameter and an inner layer of the at least two layers corresponding to the stent comprises at least one nano-carrier with a second average diameter and at least one nano-carrier with a first average diameter, wherein the outer layer corresponding to the stent and balloon provides burst release of the at least one nano-carrier with the third average diameter from the outer surface of the stent, and wherein the at least one nano-carrier with the second average diameter and the at least one nano-carrier with the first average diameter penetrate at least one layer of the plurality of layers upon coming in proximity with the target site in the body lumen over a time.

7. The drug-delivering insertable medical device of claim 5, wherein the drug-delivering insertable medical device is coated with at least two layers of the plurality of nano-carriers, wherein the outer layer of the at least two layers comprises at least one drug different from at least one drug comprised in the inner layer of the at least two layers.

8. The drug-delivering insertable medical device of claim 1, wherein the first set of nano-carriers, the second set of nano-carriers and the third set of nano-carriers comprise different drugs.

9. The drug-delivering insertable medical device of claim 8, wherein the first set of nano-carriers comprises a drug selected from a group comprising an anti-inflammatory agent and an anti-thrombogenic agent and the second set of nano-carriers comprise an anti-proliferative agent.

10. The drug-delivering insertable medical device of claim 9, wherein the drug is selected from a group comprising an anti-proliferative agent, an anti-inflammatory agent, an anti-neoplastic agent, an anti-coagulant agent, an anti-fibrin agent, an antithrombotic agent, an anti-mitotic agent, an antibiotic agent, an anti-allergic agent and an antioxidant, an anti-proliferative agent, estrogens, a protease inhibitor, antibodies, an immunosuppressive agent, a cytostatic agent, a cytotoxic agent, a calcium channel blocker, a phosphodiesterase inhibitor, a prostaglandin inhibitor, a dietary supplement, vitamins, anti-platelet aggregating agent and genetically engineered epithelial cells.

11. The drug-delivering insertable medical device of claim 9, wherein the drug is selected from a group comprising paclitaxel, sirolimus, tacrolimus, clobetasol, dexamethasone, genistein, heparin, 17 beta-estadiol, rapamycin, everolimus, ethylrapamycin, zotarolimus, ABT-578, Biolimus A9, docetaxel, methotrexate, azathioprine, vincristine, vinblastine, fluorouracil, doxorubicin hydrochloride, mitomycin and analogs thereof, miomycine, sodium heparin, a low molecular weight heparin, a heparinoid, hirudin, argatroban, forskolin, vapiprost, prostacyclin, a prostacyclin analogue, dextran, D-phe-pro-arg-chloromethylketone, dipyridamole, glycoprotein IIb/IIIa, recombinant hirudin, bivalirudin, nifedipine, colchicines, lovastatin, nitroprusside, suramin, a serotonin blocker, a steroid, a thioprotease inhibitor, triazolopyrimidine, a nitric oxide or nitric oxide donor, a super oxide dismutase, a super oxide dismutase mimetic, estradiol, aspirin, angiopeptin, captopril, cilazapril, lisinopril, permirolast potassium, alpha-interferon, and bioactive RGD.

12. The drug-delivering insertable medical device of claim 1, wherein the biological agent is selected from a group comprising excipients derived from blood, phospholipids, lipoids, steroids, vitamins, estradiol, esterified fatty acids, non estrified fatty acid, glucose, inositol, L-lactate, lipoproteins, carbohydrates, tricalcium phosphate, precipitated calcium phosphate, calcium phoshate tribasic, and substances derived from human, egg and soybean.

13. The drug-delivering insertable medical device of claim 1, wherein at least one of the biological agent and the blood excipient dissolves in a medium having a pH less than 7.4.

14. The insertable medical device of claim 1, wherein the medical condition comprises at least one of restenosis, blocked body lumen, atherosclerosis, and plaque accumulation in the body lumen.

15. The drug-delivering insertable medical device of claim 1, wherein the body lumen comprises a coronary artery.

16. The drug-delivering insertable medical device of claim 1, wherein the artery is selected from a group comprising coronary artery, peripheral arteries, carotid artery, iliac artery, and arteries below a knee.

17. The drug-delivering insertable medical device of claim 1, wherein the phospholipid is selected from a group comprising phosphatidylcholines (lecithins), phosphatidylglycerol, phosphatidylinositol, phosphatidylserine, phosphatidic acid, cardiolipin, and phosphatidylethanolamine.

* * * * *